US010208339B2

(12) United States Patent
Mir et al.

(10) Patent No.: US 10,208,339 B2
(45) Date of Patent: Feb. 19, 2019

(54) SYSTEMS AND METHODS FOR WHOLE GENOME AMPLIFICATION

(71) Applicant: Takara Bio USA, Inc., Mountain View, CA (US)

(72) Inventors: Alain-Albert Mir, Redwood City, CA (US); Thomas David Schaal, San Francisco, CA (US); Jude Dunne, Menlo Park, CA (US); Maithreyan Srinivasan, Palo Alto, CA (US)

(73) Assignee: TAKARA BIO USA, INC., Mountain View, CA (US)

( * ) Notice: Subject to any disclaimer, the term of this patent is extended or adjusted under 35 U.S.C. 154(b) by 296 days.

(21) Appl. No.: 15/047,259

(22) Filed: Feb. 18, 2016

(65) Prior Publication Data
US 2016/0304935 A1 Oct. 20, 2016

Related U.S. Application Data

(60) Provisional application No. 62/118,131, filed on Feb. 19, 2015.

(51) Int. Cl.
C12Q 1/68 (2018.01)
C12P 19/34 (2006.01)
C12Q 1/686 (2018.01)
C12Q 1/6874 (2018.01)
C12N 9/12 (2006.01)
C12Q 1/6844 (2018.01)

(52) U.S. Cl.
CPC .......... C12Q 1/686 (2013.01); C12N 9/1252 (2013.01); C12Q 1/6844 (2013.01); C12Q 1/6874 (2013.01); C12Y 207/07007 (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,130,238 A | 7/1992 | Malek et al. |
| 5,270,184 A | 12/1993 | Walker et al. |
| 5,399,491 A | 3/1995 | Kacian et al. |
| 5,455,166 A | 10/1995 | Walker |
| 5,695,934 A | 12/1997 | Brenner |
| 5,714,330 A | 2/1998 | Brenner et al. |
| 5,750,341 A | 5/1998 | Macevicz |
| 5,824,518 A | 10/1998 | Kacian et al. |
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren |
| 6,280,949 B1* | 8/2001 | Lizardi ................ C12Q 1/6844 435/6.1 |
| 6,306,597 B1 | 10/2001 | Macevicz |
| 6,316,229 B1* | 11/2001 | Lizardi ................ C12Q 1/682 435/6.1 |
| 6,432,360 B1 | 8/2002 | Church |
| 6,485,944 B1 | 11/2002 | Church |
| 6,511,803 B1 | 1/2003 | Church et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,311,794 B2 | 12/2007 | Joseph et al. |
| 7,329,492 B2 | 2/2008 | Hardin et al. |
| 7,482,120 B2 | 3/2009 | Quake et al. |
| 7,501,245 B2 | 3/2009 | Quake et al. |
| 7,622,296 B2 | 11/2009 | Joseph et al. |
| 7,668,697 B2 | 2/2010 | Volkov et al. |
| 7,833,709 B2 | 11/2010 | Joseph et al. |
| 2002/0177142 A1* | 11/2002 | Christian ............. C12Q 1/6844 435/6.12 |
| 2002/0197618 A1* | 12/2002 | Sampson ............. C12Q 1/6806 435/6.12 |
| 2006/0046265 A1 | 3/2006 | Becker et al. |
| 2008/0241951 A1 | 10/2008 | Battulga et al. |

(Continued)

FOREIGN PATENT DOCUMENTS

| | | |
|---|---|---|
| EP | 0 684 315 | 6/2002 |
| WO | WO 00018957 | 4/2000 |

(Continued)

OTHER PUBLICATIONS

Wu et al., "Performance Assessment of a Novel Two-Step Multiple Displacement Amplification-PCR Assay for Detection of Mycobacterium tuberculosis Complex in Sputum Specimens," Journal of Clinical Microbiology, vol. 50, No. 4, pp. 1443-1445. (Year: 2012).*
Berry et al.., "Barcoded Primers Used in Multiplex Amplicon Pyrosequencing Bias Amplification," Applied and Environmental Microbiology, November, vol. 77, No. 21, pp. 7846-7849. (Year: 2011).*
Adessi et al., Solid phase DNA amplification: characterisation of primer attachment and amplification mechanisms. Nucleic Acids Res. Oct. 15, 2000;28(20):E87.
Alsmadi et al., Specific and complete human genome amplification with improved yield achieved by phi29 DNA polymerase and a novel primer at elevated temperature. BMC Res Notes. Mar. 24, 2009;2:48.
Aubele et al., Degenerate oligonucleotide-primed PCR. Methods Mol Biol. 2003;226:315-8.

(Continued)

Primary Examiner — Young J Kim
(74) Attorney, Agent, or Firm — Otto C. Guedelhoefer, IV; Bret E. Field; Bozicevic, Field & Francis LLP

(57) ABSTRACT

Provided herein are systems and methods for whole genome amplification and sequencing. In particular, provided herein are systems and methods for detection of nucleic acid variants (e.g., rare variants) in limited samples.

10 Claims, 16 Drawing Sheets
Specification includes a Sequence Listing.

(56) References Cited

U.S. PATENT DOCUMENTS

| | | | |
|---|---|---|---|
| 2009/0026082 | A1 | 1/2009 | Rothberg et al. |
| 2009/0035777 | A1 | 2/2009 | Kokoris et al. |
| 2009/0127589 | A1 | 5/2009 | Rothberg et al. |
| 2009/0130720 | A1* | 5/2009 | Nelson ................ C12Q 1/6848 435/91.2 |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2012/0100549 | A1 | 4/2012 | Eshoo et al. |
| 2012/0108467 | A1 | 5/2012 | Brenner |
| 2013/0116130 | A1 | 5/2013 | Fu et al. |
| 2014/0019064 | A1* | 1/2014 | Lo ........................... G06F 19/18 702/20 |

FOREIGN PATENT DOCUMENTS

| | | |
|---|---|---|
| WO | WO 2007087312 | 8/2007 |
| WO | WO 2008051928 | 5/2008 |
| WO | WO 2012166425 | 12/2012 |

OTHER PUBLICATIONS

Aviel-Ronen et al., Large fragment Bst DNA polymerase for whole genome amplification of DNA from formalin-fixed paraffin-embedded tissues. BMC Genomics. Dec. 12, 2006;7:312.

Bennett et al., Toward the 1,000 dollars human genome. Pharmacogenomics. Jun. 2005;6(4):373-82.

Binladen et al., The use of coded PCR primers enables high-throughput sequencing of multiple homolog amplification products by 454 parallel sequencing. PLoS One. Feb. 14, 2007;2(2):e197.

Brenner et al., Gene expression analysis by massively parallel signature sequencing (MPSS) on microbead arrays.Nat Biotechnol. Jun. 2000;18(6):630-4.

Caporaso et al., Ultra-high-throughput microbial community analysis on the Illumina HiSeq and MiSeq platforms. ISME J. Aug. 2012;6(8):1621-4.

Cervantes et al., Embryonic stem cells and somatic cells differ in mutation frequency and type. Proc Natl Acad Sci U S A. Mar. 19, 2002;99(6):3586-90.

Costea et al., TagGD: fast and accurate software for DNA Tag generation and demultiplexing. PLoS One. 2013;8(3):e57521.

De Bourcy et al., A quantitative comparison of single-cell whole genome amplification methods. PLoS One. Aug. 19, 2014;9(8):e105585.

Fang et al., Minimizing DNA recombination during long RT-PCR. J Virol Methods. Dec. 1998;76(1-2):139-48.

Gardner et al., Multiplex degenerate primer design for targeted whole genome amplification of many viral genomes. Adv Bioinformatics. 2014;2014:101894.

Guatelli et al., Isothermal, in vitro amplification of nucleic acids by a multienzyme reaction modeled after retroviral replication. Proc Natl Acad Sci U S A. Mar. 1990;87(5):1874-8.

Holbrook et al., Exploring whole genome amplification as a DNA recovery tool for molecular genetic studies. J Biomol Tech. Jun. 2005;16(2):125-33.

Hou et al., Genome analyses of single human oocytes. Cell. Dec. 19, 2013;155(7):1492-506.

Huang et al., Validation of multiple annealing and looping-based amplification cycle sequencing for 24-chromosome aneuploidy screening of cleavage-stage embryos. Fertil Steril. Dec. 2014;102(6):1685-91.

Jones et al., Genome walking with 2- to 4-kb steps using panhandle PCR. PCR Methods Appl. Feb. 1993;2(3):197-203.

Jones, Sequence specific generation of a DNA panhandle permits PCR amplification of unknown flanking DNA. Nucleic Acids Res. Feb. 11, 1992;20(3):595-600.

Kasschau et al., Genome-wide profiling and analysis of Arabidopsis siRNAs. PLoS Biol. Mar. 2007;5(3):e57.

Kinde et al., Detection and quantification of rare mutations with massively parallel sequencing. Proc Natl Acad Sci U S A. Jun. 7, 2011;108(23):9530-5.

Kircher et al., Double indexing overcomes inaccuracies in multiplex sequencing on the Illumina platform. Nucleic Acids Res. Jan. 2012;40(1):e3.

Kozarewa et al., 96-plex molecular barcoding for the Illumina Genome Analyzer. Methods Mol Biol. 2011;733:279-98.

Kwoh et al., Transcription-based amplification system and detection of amplified human immunodeficiency virus type 1 with a bead-based sandwich hybridization format. Proc Natl Acad Sci U S A. Feb. 1989;86(4):1173-7.

Lage et al., et al. Whole genome analysis of genetic alterations in small DNA samples using hyperbranched strand displacement amplification and array-CGH. Genome Res. Feb. 2003;13(2):294-307.

Liu et al., Development and validation of a whole genome amplification long-range PCR sequencing method for ADPKD genotyping of low-level DNA samples. Gene. Oct. 15, 2014;550(1):131-5.

Lizardi et al., Exponential Amplification of Recombinant—RNA Hybridization Probes. Nat Biotechnol. 1988;6:1197-1202.

MacLean et al., Application of 'next-generation' sequencing technologies to microbial genetics. Nat Rev Microbiol. Apr. 2009;7(4):287-96.

Mead et al., Bst DNA polymerase permits rapid sequence analysis from nanogram amounts of template. Biotechniques. Jul. 1991;11(1):76-8, 80, 82-7.

Metzker, Sequencing technologies—the next generation. Nat Rev Genet. Jan. 2010;11(1):31-46.

Meyerhans et al., DNA recombination during PCR. Nucleic Acids Res. Apr. 11, 1990;18(7):1687-91.

Mitra et al., Fluorescent in situ sequencing on polymerase colonies. Anal Biochem. Sep. 1, 2003;320(1):55-65.

Mullis et al., Specific synthesis of DNA in vitro via a polymerase-catalyzed chain reaction. Methods Enzymol. 1987;155:335-50.

Murakawa et al., Direct detection of HIV-1 RNA from AIDS and ARC patient samples. DNA. May 1988;7(4):287-95.

Nelson, Random-primed, Phi29 DNA polymerase-based whole genome amplification. Curr Protoc Mol Biol. Jan. 6, 2014;105:Unit 15.13.

Park et al., 3' Race walking along a large cDNA employing tiered suppression PCR. Biotechniques. Apr. 2003;34(4):750-2, 754-6.

Pennisi, Genomics. Semiconductors inspire new sequencing technologies. Science. Mar. 5, 2010;327(5970):1190.

Quail et al., SASI-Seq: sample assurance Spike-Ins, and highly differentiating 384 barcoding for Illumina sequencing. BMC Genomics. Feb. 7, 2014;15:110.

Roach et al., Analysis of genetic inheritance in a family quartet by whole-genome sequencing. Science. Apr. 30, 2010;328(5978):636-9.

Robasky et al., The role of replicates for error mitigation in next-generation sequencing. Nat Rev Genet. Jan. 2014;15(1):56-62.

Robinson et al., BglII-based panhandle and reverse panhandle PCR approaches increase capability for cloning der(II) and der(other) genomic breakpoint junctions of MLL translocations. Genes Chromosomes Cancer. Aug. 2006;45(8):740-53.

Schmitt et al., Detection of ultra-rare mutations by next-generation sequencing. Proc Natl Acad Sci U S A. Sep. 4, 2012;109(36):14508-13.

Shendure et al., Accurate multiplex polony sequencing of an evolved bacterial genome. Science. Sep. 9, 2005;309(5741):1728-32.

Spits et al., Optimization and evaluation of single-cell whole-genome multiple displacement amplification. Hum Mutat. May 2006;27(5):496-503.

Telenius et al., Degenerate oligonucleotide-primed PCR: general amplification of target DNA by a single degenerate primer. Genomics. Jul. 1992;13(3):718-25.

Voelkerding et al., Next-generation sequencing: from basic research to diagnostics. Clin Chem. Apr. 2009;55(4):641-58.

Walker et al., Isothermal in vitro amplification of DNA by a restriction enzyme/DNA polymerase system. Proc Natl Acad Sci U S A. Jan. 1, 1992;89(1):392-6.

Wang et al., Clonal evolution in breast cancer revealed by single nucleus genome sequencing. Nature. Aug. 14, 2014;512(7513):155-60.

(56) References Cited

OTHER PUBLICATIONS

Weiss, Hot prospect for new gene amplifier. Science. Nov. 29, 1991;254(5036):1292-3.
Yu et al., Microfluidic whole genome amplification device for single cell sequencing. Anal Chem. Oct. 7, 2014;86(19):9386-90.
Zhang et al., Whole genome amplification from a single cell: implications for genetic analysis. Proc Natl Acad Sci U S A. Jul. 1, 1992;89(13):5847-51.
Zong et al., Genome-wide detection of single-nucleotide and copy-number variations of a single human cell. Science. Dec. 21, 2012;338(6114):1622-6.

* cited by examiner

FIG. 1

| | 1x MALBAC primer anneal: 3 4X Chr gDNA/ NTC | 1 rxn 1x | 5 rxns 5 |
|---|---|---|---|
| 1X Anneal <br> PCR program: "94 '5min" 4C fast ramp. (94C /5min)x1; (4C sit) 10 uL vol | DNA sample, 6, 18, 60pg and NTC 4X Chr. DNA | 1 | 5 |
| | 10 uM P=S 27merGGG => 0.32 uM (IDT) | 0.64 | 3.2 |
| | 10 uM P=S 27merTTT => 0.25 uM (IDT) | 0.5 | 2.5 |
| | 10X Phi29 Reaction buffer (NEB) | 1 | 5 |
| | dwater | 6.86 | 34.3 |
| | Sum | 10 | 50 |

Add 9 uLs of of each sample mix to each tube
Add water NTCs
Add 1 uL of DNA to each
94' 5min

| | 2X Phi29 mix. Assemble @ RT | 1 rxn 1x | 5 rxns 5 |
|---|---|---|---|
| 2X WGA Add 10 uL to above <br> PCR program: "Phi3hrs@40" (30C/20min)x1; (40C 3hrs)x1 (65C/10min) x1; (4C sit) 20 uL vol | 10 uL sample from above | 0 | 0 |
| | Phi29 polymerase M0269S (NEB) | 1 | 5 |
| | 10X Phi29 Reaction buffer (NEB) | 1 | 5 |
| | 50x dNTPS : Roche vial 6 FASTstart HiFi Cat 0473828 | 0.4 | 2 |
| | 10 mg/mL BSA to 0.1 mg/mL (NEB) | 0.4 | 2 |
| | dwater | 7.2 | 36 |
| | Sum | 10 | 50 |

Cycle reactions "Phi3hrs@40" on BioRad T100

| | 5x MALBAC 27 mer Preamp PCR Assemble @ RT | 1 rxn 1x | 5 rxns 5 |
|---|---|---|---|
| 3X Preamp PCR Add 10 uL to above <br> PCR program: "MAL30PCR" (95C/2min)x1; (95C/30sec) (58C /30sec) (72C/3mins) x30; (4C sit) 30 uL vol | 20 uL sample from above | 0 | 0 |
| | 100uM MALBAC 27 mer only to 0.5 uM (IDT) | 0.15 | 0.75 |
| | DNA Polymse : Roche vial 1 0.5uL / 50uL rxn Cat 047: | 0.30 | 1.50 |
| | 50x dNTPS : NEB | 0.60 | 3.00 |
| | 10x buffer: Roche vial 2 Cat 0473828401 | 2.00 | 10.00 |
| | dwater | 6.95 | 34.75 |
| | Sum | 10 | 50 |

PCR Thermal Cycle use MAL30PCR for 30 Cycles on BioRad T100

Reference unamplified (green line)

FIG. 4B
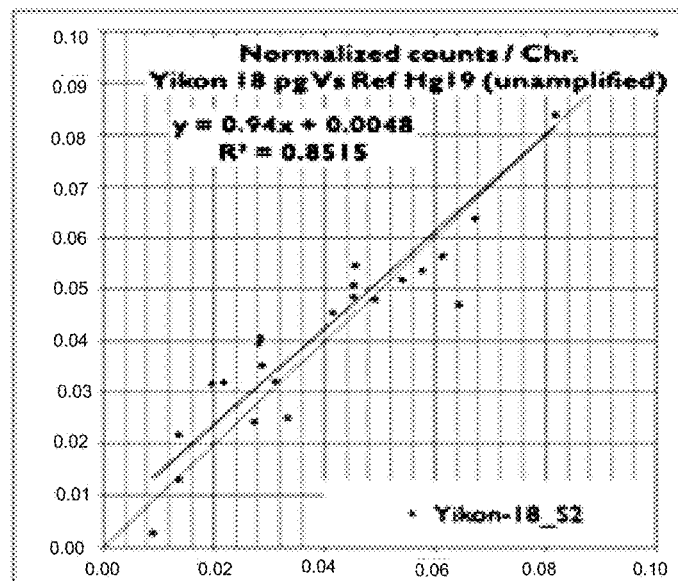
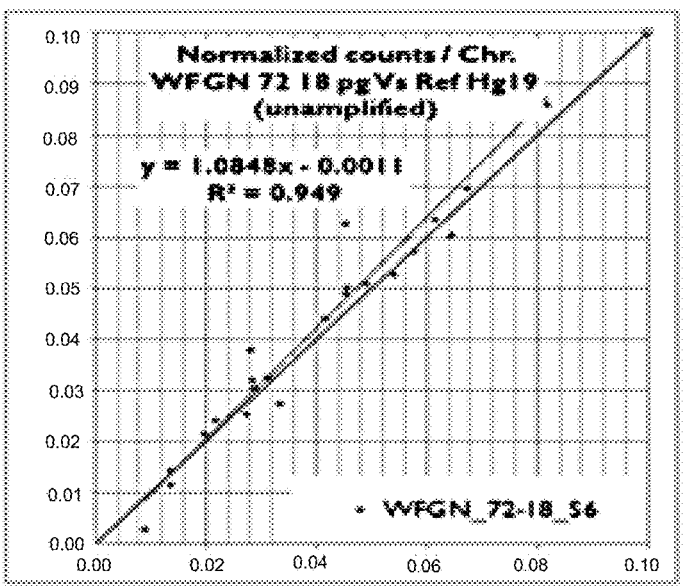
Reference unamplified (green line)

FIG. 4C
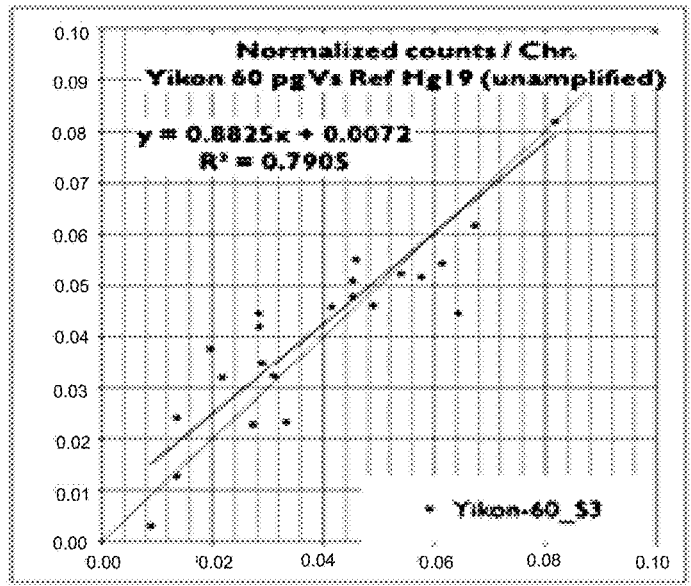
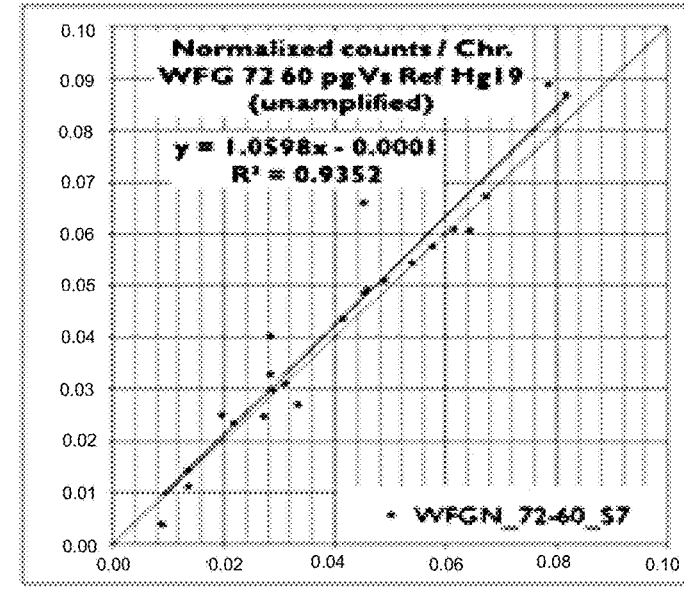
Reference unamplified (green line)

FIG. 5A

| 27 | 8 | 10 | 5 | 3 |
|---|---|---|---|---|
| MALBAC tag | MBC | SBC | 5Ns | 3G/3T |
| GTGAGTGATGGTTGAGGTAGTGTGGAG (SEQ ID NO:3) | NNNNNNNN | GTCAGTATAC (SEQ ID NO:4) | NNNNN | K*K*K | tag    Tag sequence on all WGA and PCR ends. Can also be P5 or P7 sequence. The 27 mer MALBAC tag shown MBC    8 randomized sequence bases 25% each G,A, T or C=65,536 variants SBC    In line SBC (10 bases). Each sample bears 2 separate SBC NNNNN    5 randomized sequence bases 25% each G,A, T or C

*    Phosphorothioate nuclease resistant 3' end. oligos 3' stable. Improves target specificity.

K*K*K    Anchoring bases at primer 3' end and that skews Phi29 polymerase extension from these high very high frequency triplets (in human)

FIG. 5B

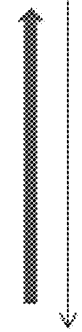

Figure showing Read 1 and Read 2 structures with the following segments:

Read 1 (left to right):
| 29 | 16 | 27 | 8 | 10 | 5 | 3 | | 3 | 5 | 10 | 8 | 27 | 16 | 24 |
|---|---|---|---|---|---|---|---|---|---|---|---|---|---|---|
| P5 (long) | Padding bases 66C | MALBAC tag | MBC | SBC | N5 | G or T | INSERT | G or T | N5 | SBC | MBC | MALBAC tag | Padding bases 66C | P7 (long) |
| AATGAT ACGGCG ATACCG AGATCT ACAC (SEQ ID NO: 5) | GAGTGAG AAGATGT GA (SEQ ID NO: 6) | GTGAGTG ATGGTTG AGGTAGT GTGGAG (SEQ ID NO: 3) | NNN NNN NN | GTCAGTA TAC (SEQ ID NO:4) | NNN NN | KKK | | KKK | NNN NN | GTCAGT ATAC (SEQ ID NO:4) | NNNNNN NN | GTGAGTG ATGGTTG AGGTAGT GTGGAG (SEQ ID NO: 3) | GAGTGAG AAGATGT GA (SEQ ID NO: 6) | CAAGCA GAAGAC GGC ATACCGA GAT (SEQ ID NO: 7) |

FIG. 8A
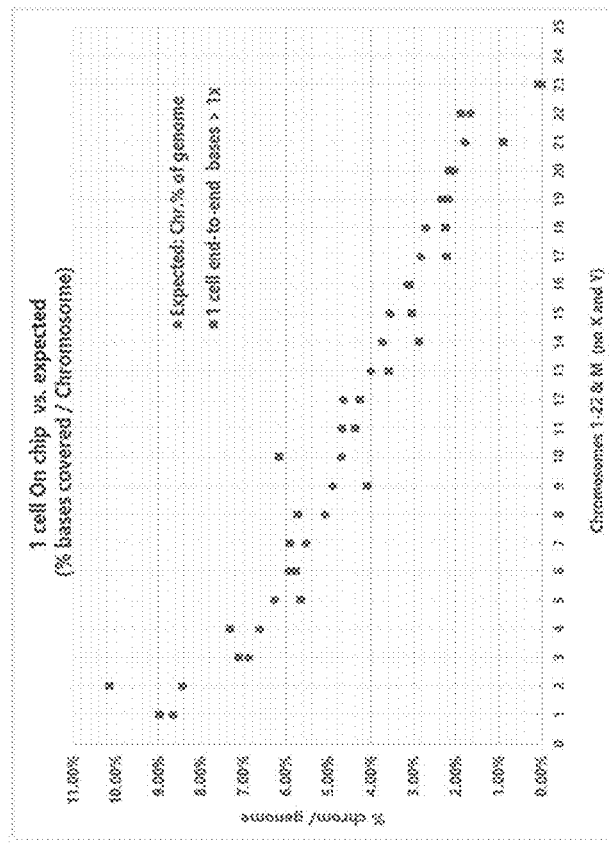

SYSTEMS AND METHODS FOR WHOLE GENOME AMPLIFICATION

CROSS-REFERENCE TO RELATED APPLICATIONS

The present application claims priority to U.S. Provisional Application 62/118,131, filed Feb. 19, 2015, which is herein incorporated by reference in its entirety.

FIELD OF THE DISCLOSURE

Provided herein are systems and methods for whole genome amplification and sequencing. In particular, provided herein are systems and methods for detection of nucleic acid variants (e.g., rare variants) in limited samples.

BACKGROUND

Geneticists are striving to characterize the genetic source of complex diseases including cancer, autoimmune and neurological disorders. However, the underlying mechanisms driving these diseases remain elusive. It is believed that both germline and somatic mutations in combination with spontaneous variants that accumulate in cells over a lifetime, are major factors that drive disease onset and reoccurrence.

Whole genome amplification (WGA) followed by next generation sequencing (NGS) is often utilized to identify nucleic acid mutations. However, existing WGA methods often introduce artifacts and errors, especially when starting with limited amounts of template. Such errors make it difficult to detect rare mutations among the noise introduced by the amplification and sequencing techniques employed.

As a consequence, a need exists to amplify DNA and RNA from limited samples (such a single cells) with high fidelity and low amounts of Template Independent DNA Amplification (TIDA).

SUMMARY

Provided herein are systems and methods for whole genome amplification and sequencing. In particular, provided herein are systems and methods for detection of nucleic acid variants (e.g., rare variants) in limited samples (e.g., single cells and/or a limited number of cells).

Embodiments of the present disclosure provide improved methods for whole genome amplification (WGA) and next generation sequencing (NGS) on limited sample. The systems and methods described herein eliminate sample cleanup steps and achieve whole genome (optionally enriched for a specific target) amplification with low no-template amplification. The systems and methods find use, for example, in detection of nucleic acid variants in samples of genomic DNA and/or RNA.

For example, in some embodiments, the present disclosure provides a method of WGA of nucleic acids, comprising: a) contacting a sample of genomic DNA with a phi29 polymerase and a heat stable DNA polymerase; and b) amplifying said genomic DNA to generate amplified DNA. In some embodiments, the contacting further comprises contacting with dNTPs, nucleic acid primers, and a buffering agent. In some embodiments, the sample of genomic DNA is a single cell sample. In some embodiments, the sample of genomic DNA is a plurality of cells. In some embodiments, the method further comprises the step of detecting one or more nucleic acid variants in said amplified DNA (e.g. including but not limited to, single nucleotide polymorphisms, single nucleotide variations, copy number variations, gene fusions, nucleic acid insertions, or nucleic acid deletions). In some embodiments, the method further comprises the step of performing a nucleic acid sequencing assay on said amplified DNA (e.g., a next generation sequencing assay). In some embodiments, the amplification and/or sequencing assays are conducted in a volume of approximately 35 to 500 nL. In some embodiments, at least subsets of said primers are specific for a nucleic acid target of interest. In some embodiments, at least a subset of said primers comprises a sample barcode, molecular barcode, label, or tag sequence. In some embodiments, a no-template control sample does not result in amplified DNA. In some embodiments, the primer comprises a single primer. In some embodiments, the amplification and said sequencing are performed in a single tube. In some embodiments, the amplification comprises both WGA (e.g., with a single primer) and PCR (e.g., with a plurality of target specific primers). In some embodiments, the reaction is performed in a microfluidic chip comprising a plurality of wells. In some embodiments, each of said wells comprises a distinct nucleic acid primer. In some embodiments, the primers generate amplicons lacking step loop structures. In some embodiments, at least one primer comprises 3' ends comprising 3-8 nucleotides designed to bind to intron/exon boundaries in a target nucleic acid. In some embodiments, the nucleotides are, for example, YAG, YAC, RTC or RTG. In some embodiments, at least one primer comprises 3' ends comprising 3-8 nucleotides that bind to repeat element consensus sequences (e.g., including but not limited to, transposons, retrotransposon, Alu1, 5' AGCT 3', LINE, SINE, interspersed repeat elements, cladistic marker sequences or transcription factor binding sites). In some embodiments, at least one primer comprises 5' ends that hybridize to a sequencing flow cell.

Further embodiments provide a system or kit, comprising: a) a phi29 polymerase; b) a heat stable polymerase; and c) at least one nucleic acid primer (e.g., wherein each of the at least one primers has the same or different nucleic acid sequences).

Additional embodiments are described herein.

DESCRIPTION OF THE FIGURES

FIG. 1 illustrates a reagent addition protocol displaying volumes and thermal conditions for WGA methods described herein.

FIGS. 4A-C illustrate observed sequenced counts per chromosome (Y axis). Expected distribution (X axis) and Pearson coefficient $R^2$ for MALBAC and methods of embodiments of the present disclosure.

FIGS. 5A-B illustrate a generalized 53 mer WGA priming sequence bearing inline SBC and MBC. FIG. 5A illustrates those primers of the general form. FIG. 5B illustrates an exemplary in line dual SBC and MBC primer-amplicon configuration.

FIGS. 8A-B illustrates sequenced bases covered/chromosome/total bases covered for and 1 and 10 cell samples respectively.

DETAILED DESCRIPTION

Figure 2A:
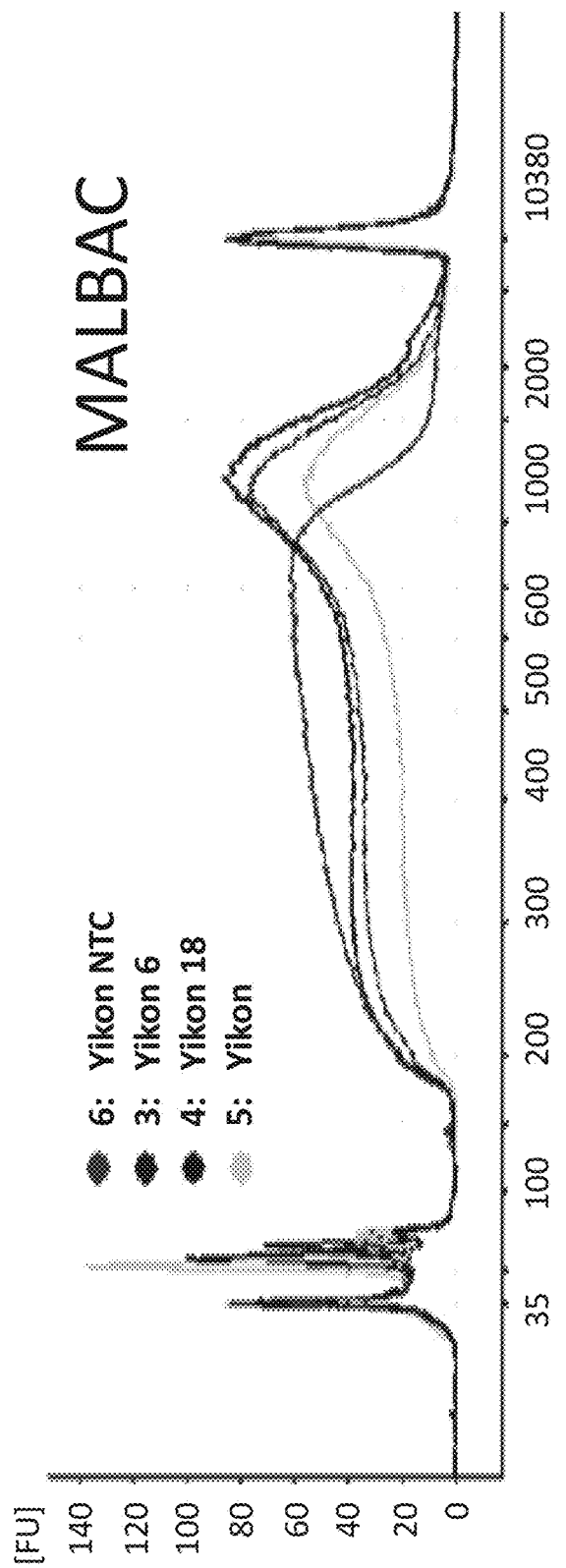
FIGS. 2A-2B illustrates the results of amplicons generated from the same DNA source Nextera "tagmented", PCR re-amplified and sized using an Agilent Hi sensitivity Bioanalyzer chip (Agilent) using MALBAC (FIG. 2A) and methods of embodiments of the present disclosure (FIG. 2B).

Provided herein are systems and methods for WGA and sequencing. In particular, provided herein are systems and methods for detection of nucleic acid variants (e.g., rare variants) in limited samples (e.g., single cells or limited numbers of cells).

Provided herein are WGA and sequencing systems and methods for detecting SNP, SNV, rare genetic variants CNV and larger scale genetic rearrangements (e.g., from limited sample amounts). The systems and methods described herein provide the advantage of analyzing single cell amounts of DNA, performing biochemical reactions (e.g., cell lysis and sample prep), and performing WGA and the Polymerase Chain Reaction (PCR) in small sample volumes (e.g., between 35 and 500 nL, although larger volumes can be utilized).

In some embodiments, the systems and methods utilize phi29 DNA polymerase, a heat stable DNA polymerase, dNTPs, primers, and a buffering agent. This formulation is employed such that only minimal volume changes and no sample cleanup are utilized. The formulation also enables addition of additional oligonucleotides to ameliorate and avoid "allele drop out" phenomena, or to selectively enrich for one or more given target regions, using a plurality of one or a pool of primers In experiments described herein, it was demonstrated that the systems and methods described herein generated similar data when compared to the Multiple Annealing and Looping Based Amplification Cycles (MALBAC) method (de Bourcy, et al., (2014) PloS one, 9, e105585; Hou, et al., (2013) Cell, 155, 1492-1506; Huang, et al., (2014) Fertil Steril; Yu, et al., (2014) Anal Chem, 86, 9386-9390; Zong, et al., (2012) Science, 338, 1622-1626). The systems and methods described herein have the added benefit of (i) employing a higher proofreading polymerase than used in MALBAC; (ii) limits the opportunity for generating undesired recurring DNA rearrangement during amplification, and (iii) decreases the opportunity to generating TIDA. Moreover, the process generates shorter amplicons than typically seen in WGA amplifications, thereby making these amplicons more amenable for subsequent PCR amplification and NGS sample preparation methodologies. This provides much needed efficiency advantages for high throughput parallel and/or sequencing analysis of large number of samples (e.g., 100, 1000, 10,000, or more samples (e.g. of single cells)).

WGA is an in vitro method employed to amplify DNA from limited samples for further molecular genetic analyses. Comprehensive human genome amplification from single cell amounts of DNA is possible. Several methods have been developed to amplify whole genomes including Primer Extension Preamplification (PEP) (Zhang et al., (1992) Proceedings of the National Academy of Sciences of the United States of America, 89, 5847-5851) and Degenerate Oligonucleotide Primed PCR (DOP-PCR) (Aubele, M. and Smida, J. (2003) Methods in molecular biology, 226, 315-318; Deng et al., (2012) Fa Yi Xue Za Zhi, 28, 41-43; Telenius et al., (1992) Genomics, 13, 718-725). Amplification yields, imbalanced amplification in addition to allele dropout (ADO) associated with these technologies have limited their broad utilization. The most recent advancement in WGA technology is multiple displacement amplification (MDA), also known as strand displacement amplification. MDA typically employs random hexamers permitting recurrent polymerase driven strand-displacement synthesis. In MDA the polymerase induces DNA strand displacement "melting" and polymerization at primer binding sites. As amplicon concentrations increase, the number of priming events also increases. The result is simultaneous priming and extension forming an interlacing network of hyper-branched DNA structures (de Bourcy et al., (2014) PloS one, 9, e105585, Gardner et al., (2014) Adv Bioinformatics, 2014, 101894; Liu et al., (2014) Gene, 550, 131-135; Nelson, J. R. (2014) Curr Protoc Mol Biol, 105, Unit 15 13). The reaction can be catalyzed by the phi29 DNA polymerase (Phi29) or by the large fragment of the Bst DNA polymerase (Bst) (Huang et al., (2014) Fertil Steril; Zong et al., Science, 338, 1622-1626). MDA type methods sometimes require many hours (e.g., >=4 hours) in order to generate a sufficient fold amplification from single cell amounts of material (Nelson, J. R. (2014), supra). All currently available WGA techniques have the limitation of generating DNA with incomplete coverage of loci throughout the genome (ADO), particularly when little amounts of starting material are used. For example, when a single cell is used, ADO rates from single-cell WGA, whether by MDA or PCR-based methods, range from 25 to 33% (Spits et al., (2006) Hum Mutat, 27, 496-503).

The Bst DNA polymerase (Bst) has recently been championed in an amplification method known as Multiple Annealing and Looping Based Amplification Cycles (MALBAC) (See e.g., de Bourcy et al., (2014) PloS one, 9, e105585; Hou et al., (2013) Cell, 155, 1492-1506; Huang et al., (2014) Fertil Steril; Yu et al., (2014) Anal Chem, 86, 9386-9390; Zong et al., (2012) Science, 338, 1622-1626)). Bst, however, has high incorporation error and low processivity rates of $1.5 \times 10^5$ and 15-25 nt respectively (Aviel-Ronen et al., (2006) BMC genomics, 7, 312; Huang et al., (1999) Sheng Wu Hua Xue Yu Sheng Wu Wu Li Xue Bao (Shanghai), 31, 379-384; Mead et al., (1991) Biotechniques, 11, 76-78, 80, 82-77). Moreover, Bst lacks a 3'→5' exonuclease activity ("proof reading activity"). Phi29 DNA polymerase, on the other hand, possesses high proofreading activity resulting in error rates 10× times lower than Bst, e.g., error and processivity rates of $1-2 \times 10^{-6}$ and 70,000 nt respectively. Simplistically, these enzymatic measurements would a priori commend the preferential use of the phi29 DNA polymerase for MDA type applications. However, a fundamental concern for WGA users is the desire to remove or ameliorate generating artifactual amplicons. In brief, low temperature MDA/WGA reactions are thought to lead to large amounts of TIDA and chimera sequences that do not belong to the original genome. These "errors" introduce artifacts into whole genome sequencing analysis. The present disclosure is not limited to a particular mechanism. Indeed, an understanding of the mechanism is not necessary to practice the disclosure. Nonetheless, it is contemplated that TIDA is the result of the random hexamer primers becoming templates for phi29 polymerase (Holbrook et al., (2005) J Biomol Tech, 16, 125-133). While other methods for WGA have been proposed (e.g., PEP and DOP) such methods are inefficient, complex and expensive and suffer their own TIDA and ADO errors. Although investigation into the phi29 TIDA phenomenon is generally lacking in the literature some authors have investigated phi29 incubation at 40° C. rather than at 30° C., phi29's optimum temperature (Alsmadi et al., (2009) *BMC Res Notes,* 2, 48). Recently, a report proposing limited Phi29 amplification at 30° C. for strictly 80 min. has recently been proposed (Wang et al., (2014) *Nature,* 512, 155-160) to limit enzyme "infidelity".

Based on those concerns, some investigators have resorted to using the lower processivity and non-proof reading enzyme Bst polymerase. This is because Bst is capable of amplification at high temperatures (55° C.) and can tolerate limited heat denaturation of DNA templates, whereas phi29 is heat labile. Moreover, some reports have demonstrated improved genomic coverage when amplification by Bst polymerase as compared to that of phi29 (Lage et al., et al. (2003) *Genome research,* 13, 294-307). However, the Bst TIDA-reduction approach (Lage et al., supra) employed nitroindole-modified primers, and the modality of artifact reduction using those expensive modifications is unknown (Lage et al., supra). The relative heat tolerance of Bst has also been harnessed using the MALBAC procedure. The MALBAC process employs five cycles of poorly understood "quasi linear" pre-amplification. MALBAC primers containing a 27 nucleotide common 5' sequence region which can loop back on themselves a, 5 N positions and a 3' trinucleotide sequence GGG or TTT sequence. In principle, such loops would be expected to display first order-like reaction kinetics rapidly forming panhandle suppression structures (Jones, D. H. (1995) *PCR Methods Appl,* 4, S195-201; Jones, (1992) *Nucleic acids research,* 20, 595-600; Jones, D. H. and Winistorfer, S. C. (1993) *PCR Methods Appl,* 2, 197-203; Park et al., (2003) *Biotechniques,* 34, 750-752, 754-756; Robinson et al. (2006) *Genes Chromosomes Cancer,* 45, 740-753) that prevent additional copying from the initial template. Suppressing amplification from previously amplified fragments is believed to reduce the amplification bias commonly associated with the uneven exponential amplification of DNA fragments by typical WGA and PCR methods (Holbrook et al., (2005) *J Biomol Tech,* 16, 125-133; WO 2012166425).

Despite this conceptual but undemonstrated panhandle suppression technique claimed in MALBAC, it has remained difficult to generically employ the MALBAC single cell technique in situations requiring both high amplicon-template fidelity and ease of use in microfluidic dispenses and devices. The major reasons for not employing "Bst-based MALBAC" are intrinsic to the polymerase incorporation error rates which include the facts that stochastic-like dNTP incorporation errors in the first cycle of MALBAC are propagated throughout subsequent amplification steps. As a consequence, MALBAC data requires comparing single cell sequencing results to those obtained from 2-3 cells within the same lineage, as well as to cells from an unrelated lineage to obtain sequencing "truth". Secondly, genome coverage at a single cell level using MALBAC is less uniform than bulk sequencing. MALBAC it is unable to detect approximately one third of SNPs compared to bulk sequencing (de Bourcy et al., (2014) *PloS one,* 9, e105585; Hou et al., (2013) *Cell,* 155, 1492-1506; Huang et al., (2014) *Fertil Steril;* Yu et al., (2014) *Anal Chem,* 86, 9386-9390; Zong et al., (2012) *Science,* 338, 1622-1626). Thirdly, in common with typical MDA procedures, MALBAC employs differing volumes of reagents for sample lysis, MDA and PCR. This renders MALBAC automation difficult for scale up when examining large numbers of single cell samples in simple microfluidic systems. Fourthly, in pre-kitted formulations, the addition of specific primers into the MDA reaction mix with the aim to amplify underrepresented genomic areas (e.g., ADO regions) or enrich for specific target sequences is not easily performed (US Pat. App. No. 20120100549 and WO 2008051928).

Investigations of varying commercial suppliers of MDA-like systems known as PicoPLEX (Rubicon Genomics), MALBAC, (Yikon Genomics), RepliG (Qiagen) Illustra GenomiPhi (GE Health Care) reveal those kits are inflexible regarding primer(s), enzyme(s) and do not permit customization/scalability for microfluidic use. Moreover, those formulations are typically "company secrets", constraining users to using predefined fixed volumes and concentrations. This renders translation of commercial kit protocols impractical or impossible in many conventional and microfluidic biochemical configurations. Therefore, a need exists for alternate MDA methods of amplifying small amounts of genomic DNA, such as from a single cell or small group of cells and limited samples in general with a strong proof reading polymerases that nevertheless generate limited amounts of TIDA.

There is generally a great need in the biological sciences for a representative, unbiased WGA method that enables: i) high polymerase processivity, strand displacement and 3'-5' "proof reading"; ii) reduced chimera and TIDA generation, iii) increased coverage/decreased ADO; iv) permits selective target enrichment; and v) permits simplified liquid handling and reagent automation in microfluidic sample preparation methodologies. More specifically, there is a great need for simplified and robust methods and kits that allow for the robust amplification of nucleic acid molecules from limited samples inputs including single cell samples. There is also a need for improved methods, compositions, systems, apparatuses and kits that allow enrichment for selective amplification of nucleic acid molecules from low input nucleic acid samples, and tagging each primer while avoiding, or minimizing, the formation of artifacts. More specifically, there is a need in the art for improved methods, compositions, systems and kits that allow for the simultaneous specific target enrichment within the MDA/WGA reaction of tens, hundreds and thousands of target-specific nucleic acid molecules in a single reaction vessel which can be used for any applicable downstream assay or analysis.

The formulation utilized in the compositions and methods described herein overcome many of those difficulties and generates data superior to MALBAC, employs a higher proofreading polymerase and a simplified process. In particular, the systems and methods described herein above avoid the artifacts and TIDA commonly observed with MALBAC and other WGA methods and provide the further advantage of the option of specifically targeting genomic regions of interest.

In some embodiments, the systems and methods described herein employ the same primer design strategies described in the MALBAC protocol to ameliorate potential inter and intra self-primer generation (Holbrook et al., (2005) *J Biomol Tech,* 16, 125-133). Uniquely, this MALBAC-styled reaction was refashioned to work using the phi29 polymerase instead of the Bst polymerase for enzyme biochemistry template fidelity reasons described above. The phi29 reaction temperatures and time were further altered so that TIDA was eliminated and NTCs were reproducibly negative (Alsmadi et al., (2009) *BMC Res Notes,* 2, 48) as judged by bioanalyzer traces. In conclusion, the MDA amplification procedure has been altered to enable use of the high fidelity and high processivity of phi29 polymerase resulting in a formulation that is easy to use for microfluidic and robotics platforms.

In some embodiments, the reaction mixture is supplemented with specific primers to enrich for specific targets as per user needs. In some embodiments, primer sequences are modified to contain tags that enable molecular and sample barcoding and permit use with instrument NGS flow cells.

The methods disclosed herein for WGA and optionally target-specific amplification may comprise conducting one or more amplification reactions. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to permit exponential increase in copy numbers of target nucleic acids. In a variation called RT-PCR, reverse transcriptase (RT) is used to make a complementary DNA (cDNA) from RNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemi-phosphorothioated primer extension product, endonuclease-mediated nicking of a hemi-modified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing. A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

In some embodiments, the systems and methods described herein are utilized in microfluidic systems. For example, in some embodiments, the SmartChip TE available from WaferGen (Fremont, Calif.) (See e.g., U.S. Pat. Nos. 7,833,709, 7,311,794, 7,622,296; herein incorporated by reference in their entirety) are utilized. Such microfluidic systems provide a plurality of reaction wells that allow high-throughput nanoliter volume reactions (e.g., from 10 to 300 nL (e.g., 10, 15, 20, 25, 30, 35, 40, 45, 50, 55, 60, 65, 70, 75, 80, 85, 90, 95, 100, 150, 200, 250, 300, 400, or 500 nL, although other volumes are specifically contemplated)).

In some embodiments, the present disclosure provides kits, systems, and software (e.g., for performing and analyzing WGA assays and/or other assays). In some embodiments, kits, and systems comprise one or more (e.g., 1, 2, 3, 4, 5, 6, 7, 8, 9, 10 or more) nucleic acid primers, primer pairs, or probes). In some embodiments, kits comprise one or more of buffers, controls, dNTPs, etc. In some embodiments, kits comprise phi29 polymerase and no additional polymerases. In some embodiments, kits comprise phi29 and an additional polymerase (e.g., Bst).

In some embodiments, reaction mixtures comprising a complex of a target nucleic acid, a primer and phi29 polymerase (e.g., alone or in combination with an additional polymerase) are provided. In some embodiments, reaction mixtures comprise a target or amplicon with one or two nucleic acid primers hybridized thereto.

Nucleic acids may also be provided on a solid support. The solid support may comprise one or more beads, plates, solid surfaces, wells, chips, or a combination thereof. The beads may be magnetic, antibody coated, protein A crosslinked, protein G crosslinked, streptavidin coated, oligonucleotide conjugated, silica coated, or a combination thereof. Examples of beads include, but are not limited to, Ampure beads, AMPure XP beads, streptavidin beads, agarose beads, magnetic beads, DNYDABEADS, MACS microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BCMAG Carboxy-Terminated Magnetic Beads.

The compositions and kits may comprise primers and primer pairs capable of amplifying target molecules, or fragments or subsequences or complements thereof. The nucleotide sequences of the target molecules may be provided in computer-readable media for in silico applications and as a basis for the design of appropriate primers for amplification of one or more target molecules.

Primers based on the nucleotide sequences of target molecules can be designed for use in amplification of the target molecules. For use in amplification reactions such as WGA or PCR, a single primer or pair of primers can be used. The exact composition of the primer sequences is not critical to the disclosure, but for most applications the primers may hybridize to specific sequences of the target molecules or universal targets under stringent conditions, particularly under conditions of high stringency, as known in the art. The pairs of primers are usually chosen so as to generate an amplification product of at least about 15 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 450 or more, 500 or more, 600 or more, 700 or more, 800 or more, 900 or more, or 1000 or more nucleotides. Algorithms for the selection of primer sequences are generally known, and are available in commercial software packages. These primers may be used in standard quantitative or qualitative PCR-based assays to assess transcript expression levels of target molecules. Alternatively, these primers may be used in combination with probes, such as molecular beacons in amplifications using real-time PCR.

One skilled in the art also appreciates that the nucleotide sequence of the entire length of the primer does not need to be derived from the target sequence. Thus, for example, the primer may comprise nucleotide sequences at the 5' and/or 3' termini that are not derived from the target molecule. Nucleotide sequences which are not derived from the nucleotide sequence of the target molecule may provide additional functionality to the primer. For example, they may provide a restriction enzyme recognition sequence or a "tag" that facilitates detection, isolation, purification or immobilization onto a solid support. Alternatively, the additional nucleotides may provide a self-complementary sequence that allows the primer to adopt a hairpin configuration. Such configurations may be necessary for certain primers, for example, molecular beacon and Scorpion primers, which can be used in solution hybridization techniques.

The probes or primers can incorporate moieties useful in detection, isolation, purification, or immobilization, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target molecule is not affected.

Examples of suitable moieties are bar codes (see above), detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer to allow detection and/or quantitation of a target polynucleotide representing the target molecule of interest. The target polynucleotide may be the expressed target molecule RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different target molecules may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the disclosure described herein include any substance which can be detected when bound to or incorporated into the target molecule. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a target polynucleotide may comprise a biotin-binding species, and an optically detectable label may be conjugated to biotin and then bound to the labeled target polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the disclosure. A variety of different coding schemes are known in the art, including fluorophores, including SCNCs, deposited metals, and RF tags.

Polynucleotides from the described target molecules may be employed as probes for detecting target molecules expression, for ligation amplification schemes, or may be used as primers for amplification schemes of all or a portion of a target molecule. When amplified, either strand produced by amplification may be provided in purified and/or isolated form.

In some embodiments, at least subsets of primers for WGA comprise a molecular bar code to track individual samples within a pool (e.g., a sequencing pool). NGS methods can produce millions even billions of reads (Metzker, M. L. (2010) Nature reviews. Genetics, 11, 31-46). Nevertheless, due to the inherent noisiness and low fidelity in a NGS single read, 20× to 100× read coverage of the same sequence is sometimes utilized to ensure the determined sequence is not erroneous. Methods known as "sample barcoding" (SBC) exist to pool multiple, uniquely identifiable sample sets colloquially known as "libraries". SBC libraries can de-multiplexed by post-image-processing bioinformatic analysis, markedly lowering costs of acquiring datasets for low complexity samples. In practice barcodes consist of DNA sequence identifiers that are appended to the ends of DNA fragments (by ligation or inclusion within an oligo by PCR). Binning reads containing the same SBC was first reported on the Roche 454 sequencing (Kasschau et al., (2007) PLoS biology, 5, e57) then the Illumina platform (Binladen et al., (2007) PLoS one, 2, e197). As sequencing yields have risen, the degree of multiplexing has also risen, from 96 barcodes (Kozarewa, I. and Turner, D. J. (2011) Methods in molecular biology, 733, 279-298), to 2167 barcodes (Caporaso et al., (2012) The ISME journal, 6, 1621-1624) and more recently the software tool TagGD can design up to 20,000-plex barcode sets (Costea et al., (2013) PloS one, 8, e57521) for the Illumina system. In the Illumina flow cell jargon, barcodes are described as "in line" if they are adjacent to the sample DNA and read from the same sequencing primer as part of the sequence read. In line SBC are obligatory to be read and "take up/consume" some of the sequencing read length (Kircher et al., (2012) Nucleic acids research, 40, e3; Indexing and Barcoding for Illumina NextGen Sequencing (2011) University of Massachusetts Medical School).

PCR processes are known to generate chimeras by recombining different templates molecules "a.k.a. jumping PCR" (Fang et al., (1998) Journal of virological methods, 76, 139-148; Meyerhans et al., (1990) DNA recombination during PCR. Nucleic acids research, 18, 1687-1691). As a result, pooled amplicon amplification methods can inadvertently introduce significant levels of sample cross-contamination (~0.3% i.e. 3 in 1000 errors) when sequencing bulk multiplex libraries. On the Illumina platform a double-indexing method, e.g., placing indexes into both of the universal adapter sequences can overcome a major error source (Kircher et al., supra) i.e. mixed cluster errors on the Illumina flow cell, Other error sources not necessarily corrected by double indexing include sporadic cross contamination introduced during oligo synthesis, sample handling missteps and some jumping PCR events. Methods such as utilizing duplex sequencing "molecular barcodes" (MBC) (Schmitt et al., (2012) Proceedings of the National Academy of Sciences of the United States of America, 109, 14508-14513) or unique identifiers such as "Safe-SeqS" are employed (Quail et al., (2014) BMC genomics, 15, 110; Kinde et al., (2011) Proceedings of the National Academy of Sciences of the United States of America, 108, 9530-9535).

Estimates of "true mutation frequencies" in normal cells generally range from 10-8 to 10-11 per position per haploid genome (Cervantes et al., (2002) Proceedings of the National Academy of Sciences of the United States of America, 99, 3586-3590; Roach et al., (2010) Science, 328, 636-639). Depending on the read quality required such as looking for rare somatic mutations, (needle in a haystack type applications) dual indexing alone may not provide a sufficient error correction methodology. Even when applying high-stringency base calling, conventional analysis using the Illumina platform has an error rate of ~9.1×10-6 errors/bp/PCR cycle. The platform error rate is more than an order of magnitude higher than the error rate reported for the Phusion DNA polymerase (NEB), a high fidelity polymerase commonly used in library construction. Random errors are also introduced during oligonucleotide synthesis, whose error rate alone is estimated at 60× more errors than obtained using Phusion PCR (Schmitt et al., (2012) Proceedings of the National Academy of Sciences of the United States of America, 109, 14508-14513). In aggregate, this indicates that mutational loads for "rare variants" using conventional NGS analysis are vastly overestimated. Consequently, NGS cannot generally be used to detect "rare variants" without error correction due to high NGS error rates from single reads. MBC methods employing technical replicates as a means of reducing errors have been proposed (Robasky et al., (2014) Nature reviews. Genetics, 15, 56-62). Those approaches propose to ligate/add a 12 nucleotide random tag sequence within the body of the in line sequencing primer (Quail et al., (2014) *BMC genomics,* 15, 110; Kinde et al., (2011) *Proceedings of the National Academy of Sciences of the United States of America,* 108, 9530-9535). Given that each end of the sample molecule can receive a randomized 12-mer tag, if a sufficiently large oligonucleotide synthesis scale is applied, 424 combinatorial variants are possible. In practice, MBC methods yield a set of sequences, each of which originated from a primordial single-stranded DNA template. Unique tag-identified duplicates are compared such that mutations are scored only when the same mutation is preset in multiple unique tags. (If a NextSeq 500 generates ~400×106 reads, this indicates each read could be individually labelled by 1 of ~700,000 unique sequencing identifiers. (If N8, each read could be individually labelled by ~10 unique MBC). In summary, it is calculated that this dual molecular barcoding approach represents a 10 million-fold error improvement over the 3.8×10-3 error value obtained using standard Illumina methods (Schmitt et al., (2012) *Proceedings of the National Academy of Sciences of the United States of America,* 109, 14508-14513. The same error correction can be achieved by ordering oligonucleotides bearing the random N sequence stretch manufactured using premixed equimolar concentrations of G, A T and C phosphoramidites during oligonucleotide manufacture. There are multiple examples of NGS error reduction (US 20120108467) approaches in the patent literature including molecular counting (WO 2007087312) and stochastic labelling (US 20130116130) respectively.

Instructions for using the kit to perform one or more methods of the disclosure can be provided, and can be provided in any fixed medium. The instructions may be located inside or outside a container or housing, and/or may be printed on the interior or exterior of any surface thereof. A kit may be in multiplex form for concurrently detecting and/or quantitating one or more different target polynucleotides representing the expressed target molecules.

Devices useful for performing methods of the disclosure are also provided. The devices can comprise means for amplifying and/or sequencing a genome or target molecules thereof, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target molecules used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection component.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the presence or absence of the target molecules being studied with a prognosis of disease outcome. Such means may comprise one or more of a variety of correlative techniques, including lookup tables, algorithms, multivariate models, and linear or nonlinear combinations of expression models or algorithms. The data may be converted to one or more likelihood scores, reflecting likelihood that the patient providing the sample may exhibit a particular disease outcome. The models and/or algorithms can be provided in machine readable format and can optionally further designate a treatment modality for a patient or class of patients.

The device also comprises output means for outputting the disease status, prognosis and/or a treatment modality. Such output means can take any form which transmits the results to a patient and/or a healthcare provider, and may include a monitor, a printed format, or both. The device may use a computer system for performing one or more of the steps provided.

The methods disclosed herein may also comprise the transmission of data/information. For example, data/information derived from the detection and/or quantification of the target may be transmitted to another device and/or instrument. In some instances, the information obtained from an algorithm may also be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

EXPERIMENTAL

Example 1

This example describes an exemplary whole genome amplification method performed in tubes. FIG. 1 shows an overview of the amplification methods.

Three oligonucleotides (described in Table 1) known as: (MALBACN53G); (MALBACN543T) and (MALBAC 27) were ordered from Integrated DNA Technology.

TABLE 1

| Oligonucleotides | |
|---|---|
| 1. Name | Sequence |
| MALBACN53G | GTGAGTGATGGTTGAGGTAGTGTGGAGNNNNNG*G*G (SEQ ID NO: 1) |
| MALBACN543T | GTGAGTGATGGTTGAGGTAGTGTGGAGNNNNNT*T*T (SEQ ID NO: 2) |
| MALBAC 27 | GTGAGTGATGGTTGAGGTAGTGTGGAG (SEQ ID NO: 3) |

Note:
"*" indicates a sulphur modified phosphodiester bond (phosphorothioate), and "N" indicates an equimolar concentration of G, A, T and C were introduced into oligonucleotides during manufacture.

The MALBAC 27 sequence is present on both ends of the resultant WGA amplicon. Phi29 polymerase, buffer and BSA were purchased from NEB; dNTPs and PCR components were purchased from Roche. MALBACN53G and MALBACN53T were employed at 0.32 and 0.25 µM, respectively. DNA 6, 18 or 60 pg., (mass equivalent to 1, 3 and 10 human genomes respectively) was annealed in 10 µL. A second 10 µL aliquot containing WGA reaction components at 2× concentration (see FIG. 1 for components) was added (stacked) on top of the first 10 µL reaction. A third 10 µL aliquot permitting PCR to occur (Hi Fi DNA polymerase and Buffer, Roche) was added. The final volume consisting of 3×10 µL aliquot dispenses was formed. An NTC consisting of passaging water through the process was performed. Base-level and limited Phi29 amplification was performed at 30° C. for 20 min. followed by 3 hours at 40° C. to minimize TIDA (Alsmadi et al., (2009) BMC Res Notes, 2, 48), and decrease amplicon length, the propensity for undesired intra-primer extension and recurrent preamplification from existing amplicons. 40° C. was chosen to both limit processivity while not inhibiting any amplicon panhandle effects (Jones, D. H. (1995) PCR Methods Appl, 4, S195-201; Jones, D. H. and Winistorfer, S. C. (1993) PCR Methods Appl, 2, 197-203; Robinson et al., (2006) Genes Chromosomes Cancer, 45, 740-753). PCR was performed using a single primer (US Pat. App. No. 20120100549) to amplify from both ends.

Reaction products were purified from low MW reaction products and reaction components using AMPure Beads (Beckman) to 0.8× concentration (twice). The same DNA samples were amplified using the MALBAC protocol as per manufacturer's instructions (Yikon Genomics). All samples were treated by standard Nextera XT tagmentation processes (Illumina). Tagmentation reactions were sized on a Bioanalyzer Hi Sensitivity Chip (Agilent) and sequenced via a single MiSeq 250 bp sequencing run (SeqMatic Corporation, Fremont).

Figure 2B:
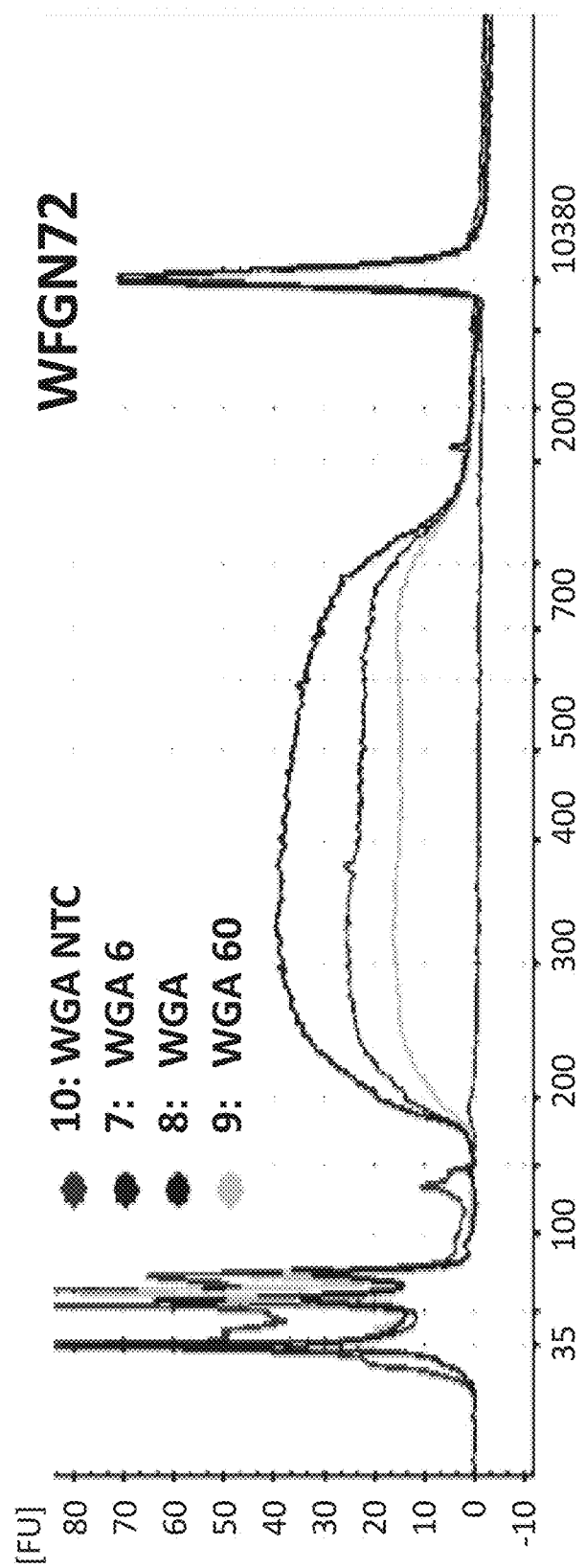

FIGS. 2a and 2b illustrate bioanalyzer sizing traces generated using MALBAC and the compositions and methods described herein, respectively. The MALBAC procedure generated a greater proportion of large fragmented higher MW material and NTC amplicons that were not observed using the compositions and methods described herein. In this example, NTC amplicons were observed in the MAL-BAC Nextera prep. NTC amplification was not observed in material prepared using the compositions and method of embodiments of the present disclosure.

WGA in nL Volume Reaction Vessels:

A WGA method was performed in Wafergen in nL volume reaction vessels. 50 nL volumes containing "1" or "10" U937 cells; 6 or 60 pg of U937 gDNA (prepared from bulk U937 tissue culture cells using Qiagen DNA preparation column), or a NTC were dispensed into 108 wells of a 5184-well "deep well" (350 nL) chip using a Wafergen Multiple Sample Nano Dispenser (MSND). All samples were dispensed in 10% glycerol. 5 separate chips were examined in this manner. Chips were sealed with optical grade sealant covers and frozen at −80 C. At a later time (7 days later) chips were thawed at room temperature for 10 mins. The MALBAC primers (100 nL, described earlier) were added in the presence of 40 ug Proteinase K (Ambion). A sealant cover was added and chips were incubated at 50 C/25 mins, 95 C/20 mins; 37 C 5 mins followed by a 4 C hold. The Phi29 amplification step was performed by addition of 50 nL (scaled using concentrations described in FIG. 1). The Phi29 amplification step was followed with a PCR reaction also performed as per FIG. 1 but with the modification that EvaGreen DNA binding dye (Biotium) was added to 1× concentration.

Figure 6:
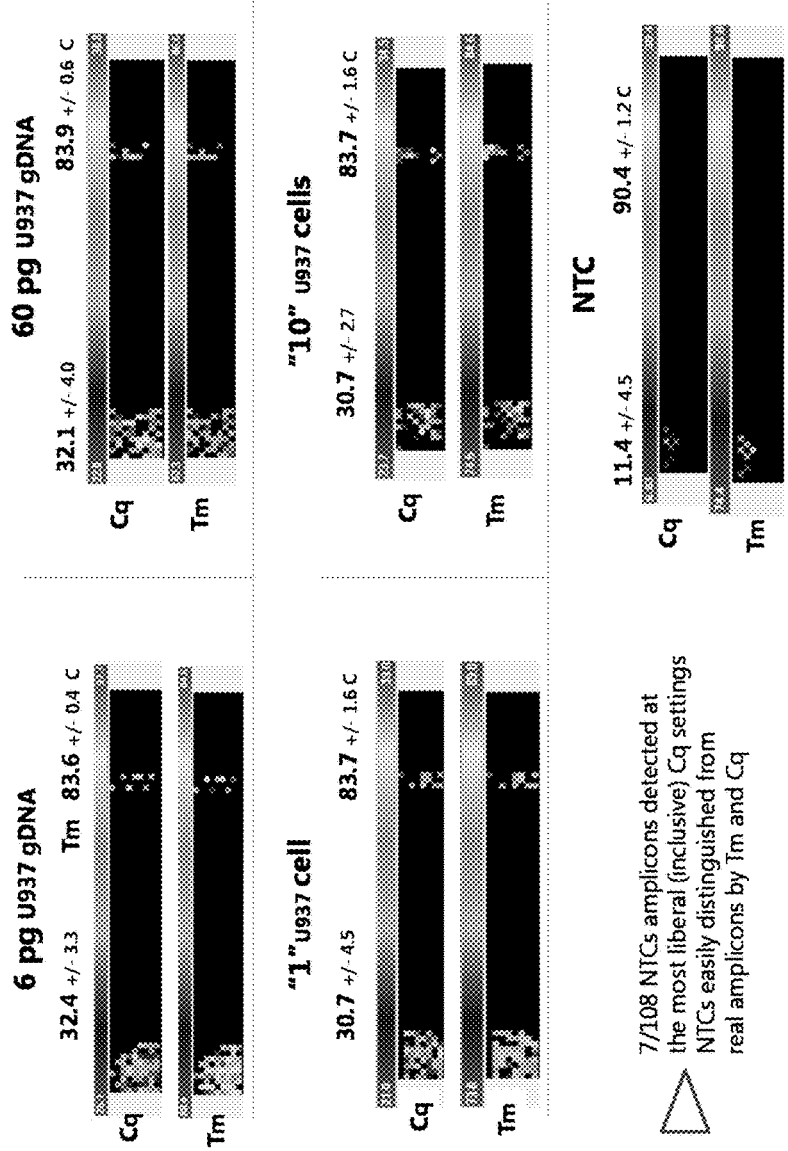
FIG. 6 illustrates in chip WGA Cq and Tm heat maps for 6 and 60 pg of gDNA positive control (1 and 10 cell equivalents) and individual 1 and 10 cell samples as dispensed in the chip for WGA methods of embodiments of the present disclosure.
Figure 7A:
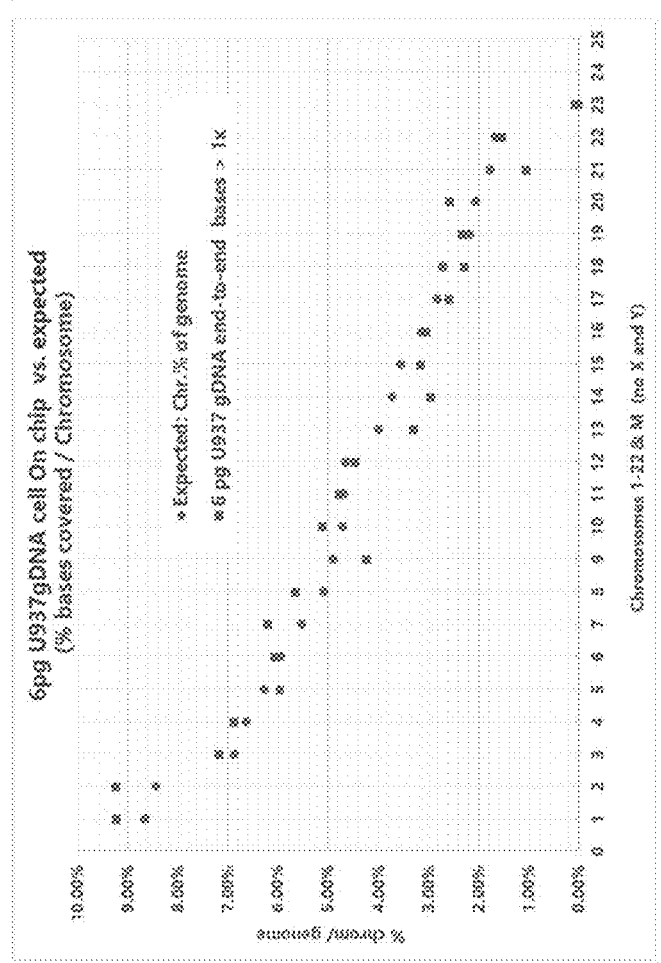
FIGS. 7A-B illustrate sequenced bases covered/chromosome/total bases covered for U937 gDNA (positive control).
Figure 7B:
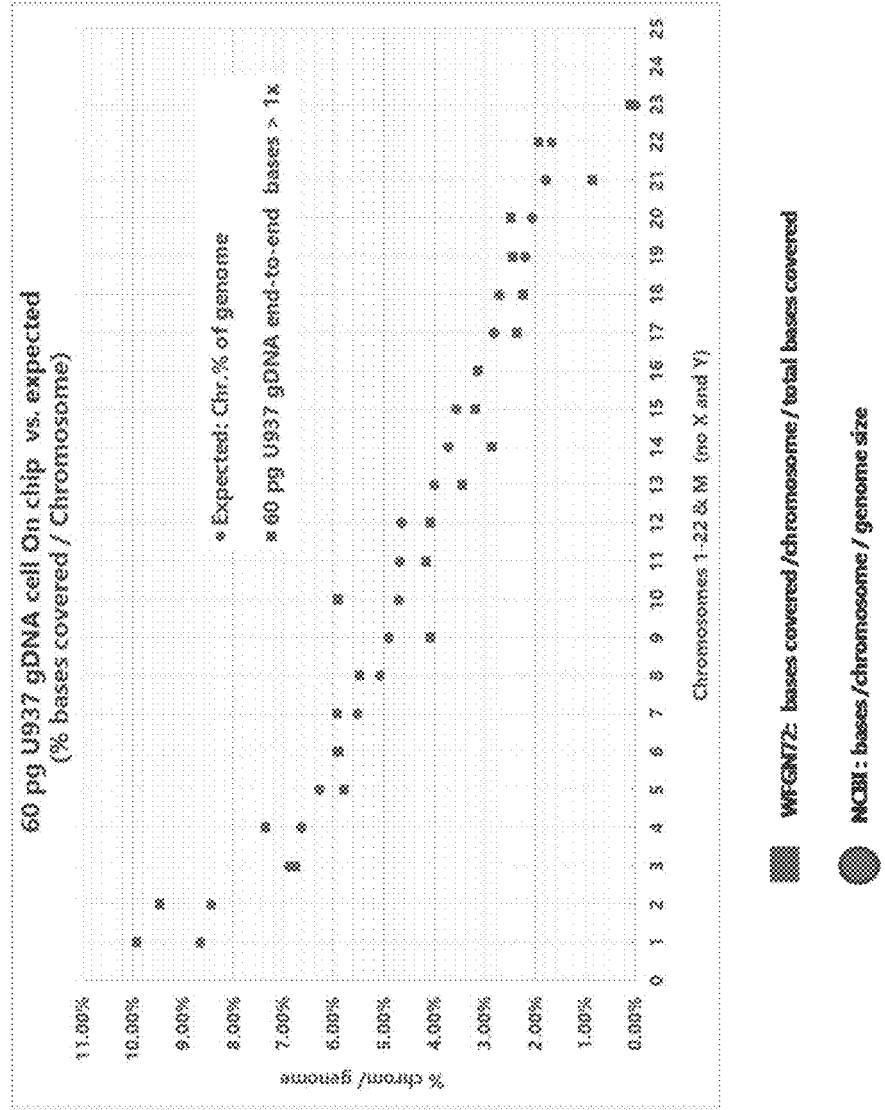
Figure 8B:
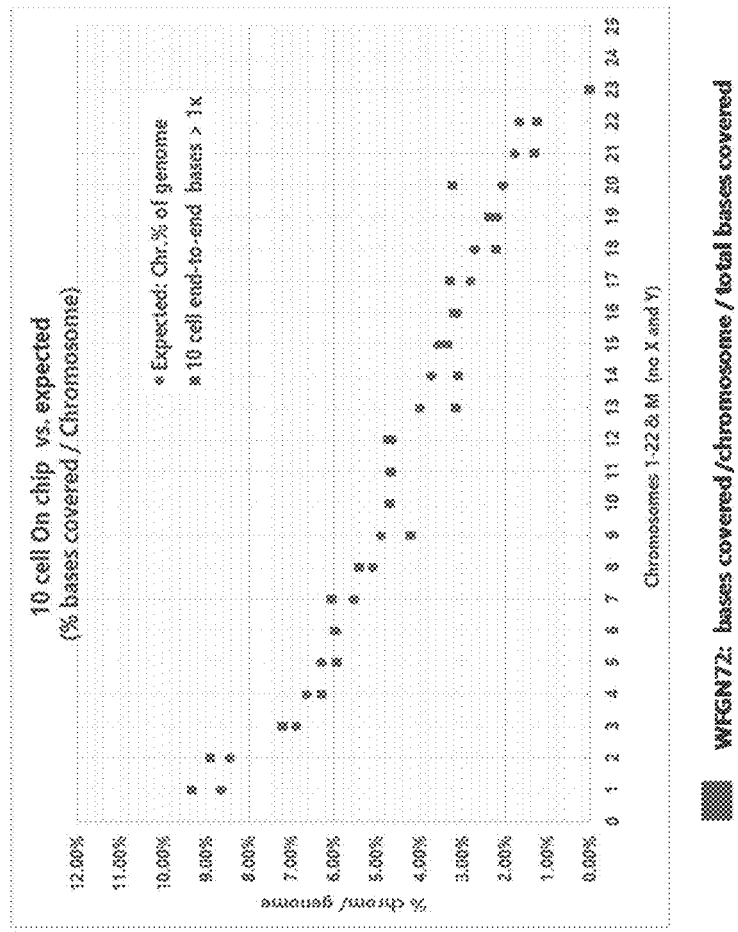

PCR thermal cycling was performed using a Wafergen Smart Cycler. Reactions in all 5184 wells were monitored for PCR amplicon production via Cq and Tm measurement. Data was deconvoluted from the 350 nL chips using Wafergen qPCR software in combination with Excel. Wafergen qPCR software amplification signals cutoffs were set to the highest leniency in an attempt to detect as many NTC signals as possible. The total volume in each reaction was approximately 250 nL. FIG. 6 provides in chip Cq and Tm heat maps for 6 and 60 pg of gDNA positive control (1 and 10 cell equivalents) and individual 1 and 10 cell samples as dispensed in the chip. A NTC demonstrates the back ground level of amplification is very low and easily distinguished form test and positive control samples.

The contents of each chip were collected by centrifugation. On chip amplicons were Nextera treated and prepared for sequencing using an Illumina MiSeq sequencer. FIGS. 7A-B and 8A-B demonstrate sequenced bases covered/chromosome/total bases covered for U937 gDNA (positive control) and 1 and 10 cell samples respectively. In general there is close alignment between expected (NCBI reference) and U937 (cancer cell line) chromosome read distribution. The chromosome level distribution difference between expected and observed reads may represent expected genomic differences between the cancerous U937 cell line and the NCBI reference human genome.

Figure 3A:
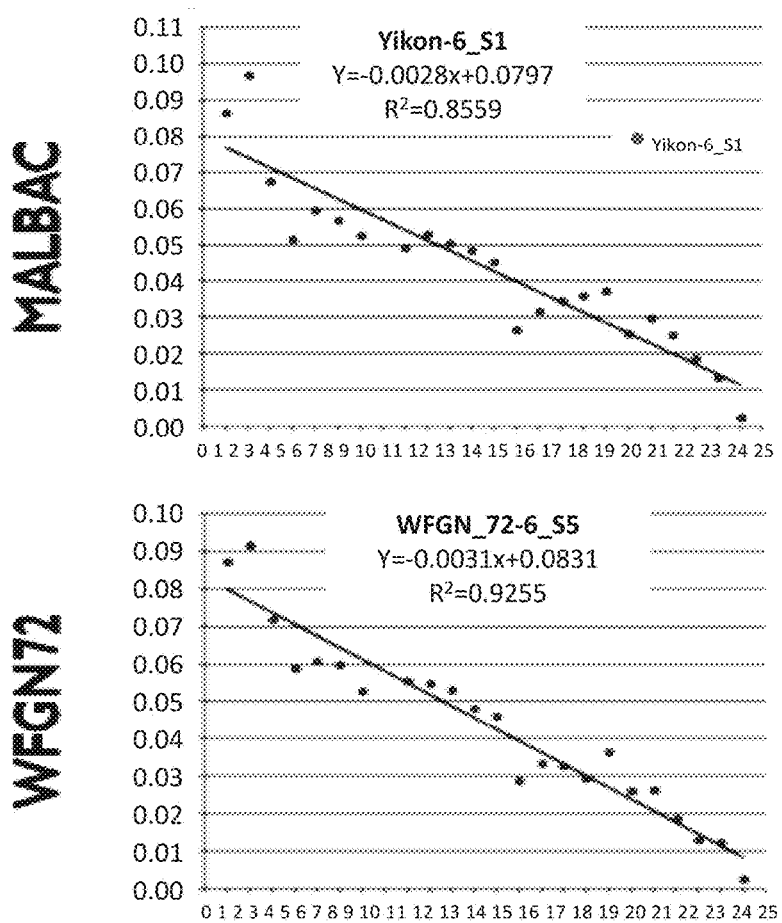
FIGS. 3A-C illustrate observed sequenced counts (Y axis) per chromosome (X axis) and a Pearson coefficient ($R^2$) for MALBAC and method of embodiments of the present disclosure.
Figure 3B:
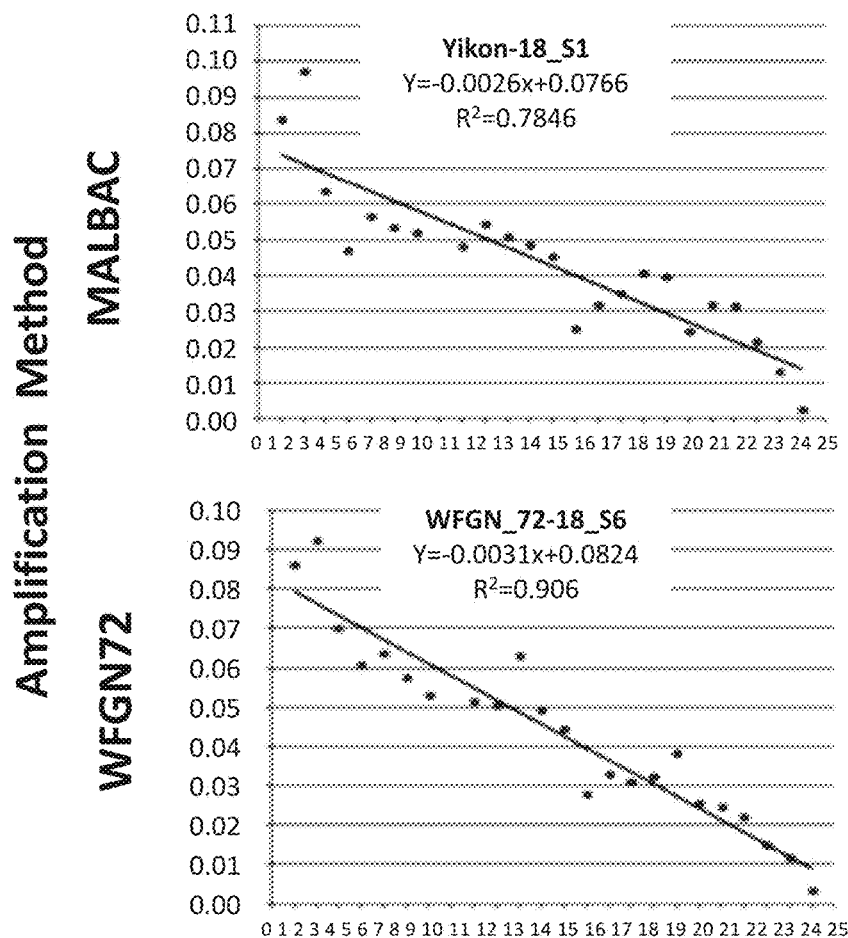
Figure 3C:
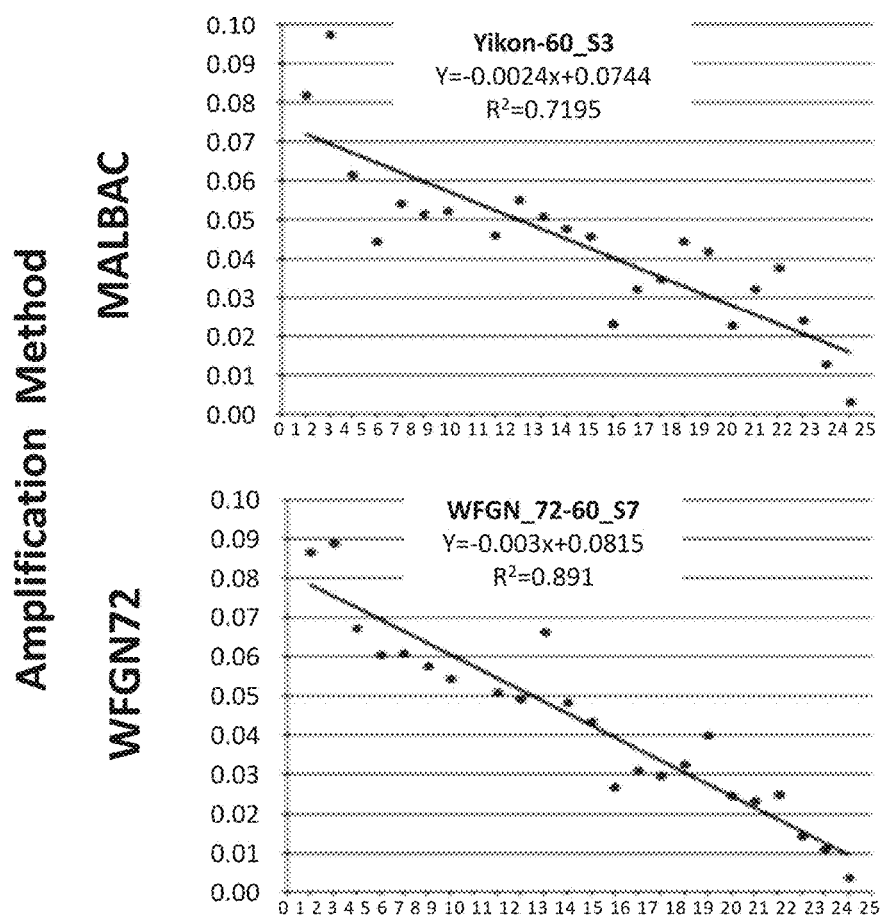
Figure 4A:
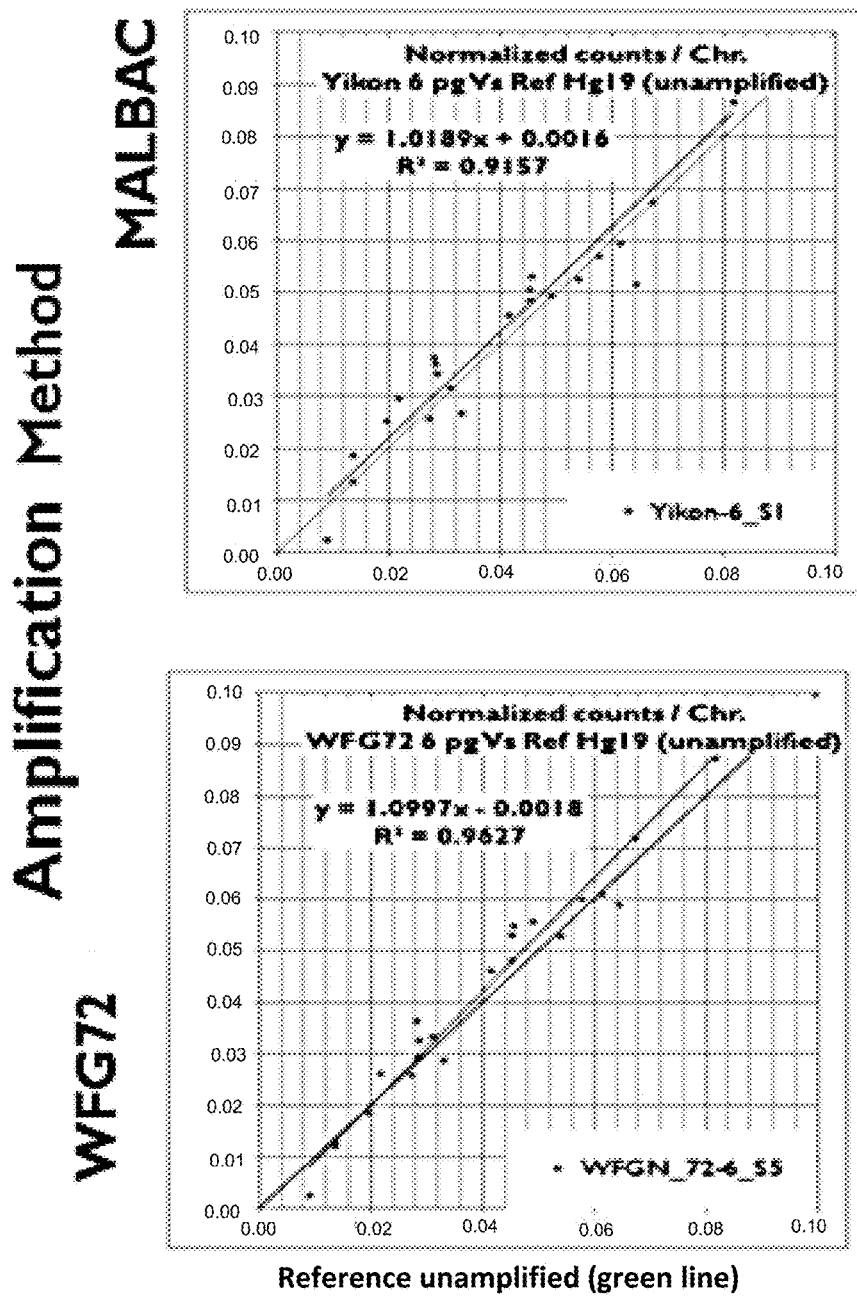

Process Sequencing Results:

Data reads across chromosomes (Chr.) was examined for both the systems and methods described herein and MALBAC using the same DNA sample (XXXX.arr(X)x4,(Y)x0) was obtained from the Coriell institute. Separate samples were barcoded and prepared using Nextera and sequenced using a sequencing MiSeq instrument. The FASTQ files from the same sequencing run were aligned to the human genome. In brief, it is known that human Chr. are named in order of their length with Chr. 1 being longer than Chr. 2 etc. The lengths of each Chr. were obtained from NCBI. FIGS. 3A-C illustrate the method at each concentration (6, 18 and 60 pg.), a plot of mapped reads per Chr. versus Chr. number (surrogate for length) was drawn. FIGS. 4A-C compares sequenced counts per chromosome for both methods (6, 18 and 60 pg.). The reference line plots the reference unamplified counts for an unamplified human genome on a per Chr. basis. The black line indicates how well each method input matches that reference. The $R^2$ coefficients are more linear between 6-to-60 pg. inputs than the equivalent MALBAC $R^2$.

Across all sample inputs the $R^2$ correlation coefficient between expected and observed slopes decreased with increased input. This indicates that a common reagent depletion effect may be occurring as the sample input concentration increases. This "reagent depletion" effect was less pronounced for the compositions and methods of embodiments of the present disclosure at all concentrations than for the MALBAC procedure. In broad summary, the method described herein generates equivalent data as MALBAC, using a higher proofreading polymerase and a simplified process.

In some embodiments, each sample in a smart chip engages with a unique pairing of WGA priming oligonucleotides that bear SBC pre-synthesized in the primer sequences. A cost effective mode of achieving 5184 unique combinations of P5 and P7 bearing SBC in a 72×72 chip is to add (preprint) P5 engageable oligos bearing a common SBC to all wells in column 1. Column 2 receives a separate common SBC with P5 engageable ends. This will be continued to column 72. Each column will contain 1 of 72 column unique SBC with P5 engageable ends. In the same manner, each row in the chip will receive a P7 engageable oligo with SBC 73 in row 1, SBC 74 in row 2 etc. to row 72. This approach produces an intersection of P5 and P7 oligos with 2 separate SBC oligos. Only 144 separate 72 columns× 72 row oligos need to be designed to yield 5184 unique SBC barcode combinations. It will be obvious to those knowledgeable in the art that the engageable tag sequence can be a variety of sequence identities including Ion Torrent PGM sequencing adaptors (A and P1) or other tags permitting further amplification such as T7 DNA polymerase binding sites (Zhu, B. (2014) Frontiers in microbiology, 5, 181; Van Gelder et al., (1990) Proceedings of the National Academy of Sciences of the United States of America, 87, 1663-1667) for subsequent microarray or a variety of other genetic analyses.

Creating the SBC matrix before sample is added (preprinted) decreases the number of stacking biochemistry reactions customers must perform. This makes the system more robust. It decreases R & D investigative investment costs. It also enables poor oligo syntheses to be rapidly identified for QC purposes. Unique pairings of SBC can be added in the 1× or 2× reaction mixtures described in FIG. 1. FIG. 5A illustrates those primers of the general form: (SEQ ID NO: 3) GTGAGTGATGGTTGAGGTAGTGTGGAG (SBC 6-10mer)(MBC; N6-N10)(N5-KKK), where K=G or T. FIG. 5B illustrates an exemplary in line dual SBC and MBC primer-amplicon configuration. The 27 mer MALBAC or other tag sequence is present on the end of all WGA and PCR amplicons to incorporate this sequence as a component of a custom primer. This avoids sequencing unwanted tag sequence. FIG. 5B shows elongating the MALBAC sequence by 16 padding bases to bring its Tm to ~65 C (in a Mg2+ free milieu). FIG. 5B illustrates the 16 bases of padding sequence 5' of the MALBAC sequence plus ~5 bases of the MALBAC sequence can be used to attach Illumina P5 and P7 flow cells sequences in bulk, off chip.

The elongated MALBAC primer is manually added to ports 12 and 14 of a MiSeq cartridge and its equivalent cartridge positions used in Next Seq and HiSeq systems. This primer binds upstream of a sample barcode and includes the SBC and MBC sequence within read 1. The reverse complement of the elongated MALBAC primer (Read 2) is added to ports 13 in a MiSeq and its equivalent cartridge positions used in Next Seq and HiSeq systems. This primer binds upstream of a sample barcode and includes SBC and MBC sequence distinct from read 2. SBC and MBC are bioinformatically de-multiplexed by end users.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A method of whole gene amplification (WGA), the method comprising:
   a) combining:
      a sample of genomic DNA template;
      a phi29 polymerase;
      nucleic acid primers; and
      dNTPs;
      into a reaction mixture under conditions sufficient for genomic DNA template-directed extension of the nucleic acid primers; and
   b) amplifying the extended nucleic acid primers in the reaction mixture with a thermostable DNA polymerase to generate amplified whole genome DNA,
   wherein said combining and amplifying are performed in a single vessel.

2. The method of claim 1, wherein said sample of genomic DNA is a single cell sample.

3. The method of claim 1, wherein said sample of genomic DNA is a plurality of cells.

4. The method of claim 1, further comprising the step of detecting one or more nucleic acid variants in said amplified whole genome DNA.

5. The method of claim 1, wherein said method further comprises the step of performing a nucleic acid sequencing assay on said amplified whole genome DNA.

6. The method of claim 1, wherein said amplification is conducted in a volume of 35 to 500 nL.

7. The method of claim 1, wherein at least a subset of said primers are specific for a nucleic acid target of interest.

8. The method of claim 1, wherein at least a subset of said primers comprises a sample barcode, molecular barcode, label, or tag sequence.

9. The method of claim 1, wherein said vessel is a well of a microfluidic chip comprising a plurality of wells.

10. The method of claim 9, wherein each of said wells comprises a distinct nucleic acid primer.

* * * * *

UNITED STATES PATENT AND TRADEMARK OFFICE
CERTIFICATE OF CORRECTION

PATENT NO. : 10,208,339 B2
APPLICATION NO. : 15/047259
DATED : February 19, 2019
INVENTOR(S) : Alain-Albert Mir et al.

Page 1 of 1

It is certified that error appears in the above-identified patent and that said Letters Patent is hereby corrected as shown below:

In the Claims

Claim 1 replace "1. A method of whole gene amplification (WGA), the method comprising:" with -- 1. A method of whole genome amplification (WGA), the method comprising: -- (Column 23, Lines 28-29).

Signed and Sealed this
Ninth Day of August, 2022

Katherine Kelly Vidal
*Director of the United States Patent and Trademark Office*

SEQUENCE LISTING

```
<160> NUMBER OF SEQ ID NOS: 7

<210> SEQ ID NO 1
<211> LENGTH: 35
<212> TYPE: DNA
<213> ORGANISM: Artificial sequence
<220> FEATURE:
<223> OTHER INFORMATION: DNA Primer
<220> FEATURE:
<221> NAME/KEY: misc_feature
<222> LOCATION: (28)..(32)
<223> OTHER INFORMATION: N= A, C, T, or G

<400> SEQUENCE: 1
gtgagtgatg gttgaggtag tgtggagnnn nnggg                              35

<210> SEQ ID NO 2
<211> LENGTH: 35
<212> TYPE: DNA
<213> ORGANISM: Artificial sequence
<220> FEATURE:
<223> OTHER INFORMATION: DNA primer
<220> FEATURE:
<221> NAME/KEY: misc_feature
<222> LOCATION: (28)..(32)
<223> OTHER INFORMATION: N= A, C, T, or G

<400> SEQUENCE: 2
gtgagtgatg gttgaggtag tgtggagnnn nnttt                              35

<210> SEQ ID NO 3
<211> LENGTH: 27
<212> TYPE: DNA
<213> ORGANISM: Artificial sequence
<220> FEATURE:
<223> OTHER INFORMATION: DNA primer

<400> SEQUENCE: 3
gtgagtgatg gttgaggtag tgtggag                                       27

<210> SEQ ID NO 4
<211> LENGTH: 10
<212> TYPE: DNA
<213> ORGANISM: Artificial sequence
<220> FEATURE:
<223> OTHER INFORMATION: DNA primer

<400> SEQUENCE: 4
gtcagtatac                                                          10

<210> SEQ ID NO 5
<211> LENGTH: 28
<212> TYPE: DNA
<213> ORGANISM: Artificial sequence
<220> FEATURE:
<223> OTHER INFORMATION: DNA primer
```

```
<400> SEQUENCE: 5
aatgatacgg cgataccgag atctacac                                    28

<210> SEQ ID NO 6
<211> LENGTH: 16
<212> TYPE: DNA
<213> ORGANISM: Artificial sequence
<220> FEATURE:
<223> OTHER INFORMATION: DNA primer

<400> SEQUENCE: 6
gagtgagaag atgtga                                                 16

<210> SEQ ID NO 7
<211> LENGTH: 24
<212> TYPE: DNA
<213> ORGANISM: Artificial sequence
<220> FEATURE:
<223> OTHER INFORMATION: DNA primer

<400> SEQUENCE: 7
caagcagaag acggcatacg agat                                        24
```